United States Patent [19]
Tolson

[11] Patent Number: 5,928,468
[45] Date of Patent: Jul. 27, 1999

[54] HIGH PRESSURE GLUE INJECTION DEVICE

[76] Inventor: John Thomas Tolson, 5390 Plum St., Fort Worth, Tex. 76148

[21] Appl. No.: 08/969,949

[22] Filed: Nov. 25, 1997

Related U.S. Application Data

[63] Continuation-in-part of application No. 08/544,557, Oct. 18, 1995, abandoned.

[51] Int. Cl.⁶ ..................................................... B05C 11/00
[52] U.S. Cl. ........................... 156/578; 156/94; 144/330; 411/395
[58] Field of Search .................................. 156/575, 578, 156/94, 305, 547; 144/330; 264/263; 411/395

[56] References Cited

U.S. PATENT DOCUMENTS

| | | | |
|---|---|---|---|
| 131,408 | 9/1872 | Peacock . | |
| 2,040,126 | 5/1936 | Grieve | 144/309 |
| 2,570,588 | 10/1951 | Nylund | 144/309 |
| 3,352,336 | 11/1967 | Smith | 144/310 |
| 3,892,621 | 7/1975 | Salonen | 156/513 |
| 4,132,516 | 1/1979 | Story | 156/94 X |
| 4,420,358 | 12/1983 | Kindt . | |
| 4,555,286 | 11/1985 | Orisaka et al. | 156/94 |
| 4,780,162 | 10/1988 | Forler et al. | 156/94 |
| 4,826,373 | 5/1989 | Nakano | 411/82 |
| 4,865,229 | 9/1989 | Schneider | 222/325 |
| 4,869,403 | 9/1989 | Bruning | 222/327 |
| 4,976,372 | 12/1990 | Rogers, Jr. | 222/324 |
| 5,115,844 | 5/1992 | Hanson | 144/2 R |
| 5,178,712 | 1/1993 | Sakai et al. | 156/305 X |
| 5,214,987 | 6/1993 | Fenton | 81/460 |
| 5,249,716 | 10/1993 | Sullivan | 282/568 |
| 5,249,899 | 10/1993 | Wilson | 411/82 |
| 5,370,273 | 12/1994 | Rohloff et al. | 222/145 |

FOREIGN PATENT DOCUMENTS 779294  7/1957  United Kingdom .

OTHER PUBLICATIONS

K–P Manufacturing Co, Minneapolis, Catalogue Published 1984 Pages Showing Grease Gurus No. 3–5486–35582 (p. 2); Grease Fitting 3–5331–35368: Grease Gun Hose & Accessories Parts 3–2015–3212).

National Industries Corp., Catalogue (Lowell, Michigan) Published 1984 Inflation Needles Part No. 3197.

KP Manufacturing Co, Minneapolis, Catalogue Published 1984 p. 4 Part Nos. 3–14220/2 Grease Injector Needle.

*Primary Examiner*—James Engel
*Attorney, Agent, or Firm*—Robert W.J. Usher

[57] ABSTRACT

An adaptor for injecting glue under high pressure into a joint to includes a shank portion with a self tapping external thread tapering from a connecting portion having an internal connecting thread for attachment to a zerk and radially outward wings, forming fingerpieces by which the shank portion can be rotated. An internal glue passageway extends completely through the adapter. A restorer's kit includes a supply of adapters, zerks, a high pressure lever action hydraulic gun for glue, a flexible high pressure connecting hose and zerk coupling, a veneer needle and a supply of dowel form wooden plugs.

9 Claims, 2 Drawing Sheets

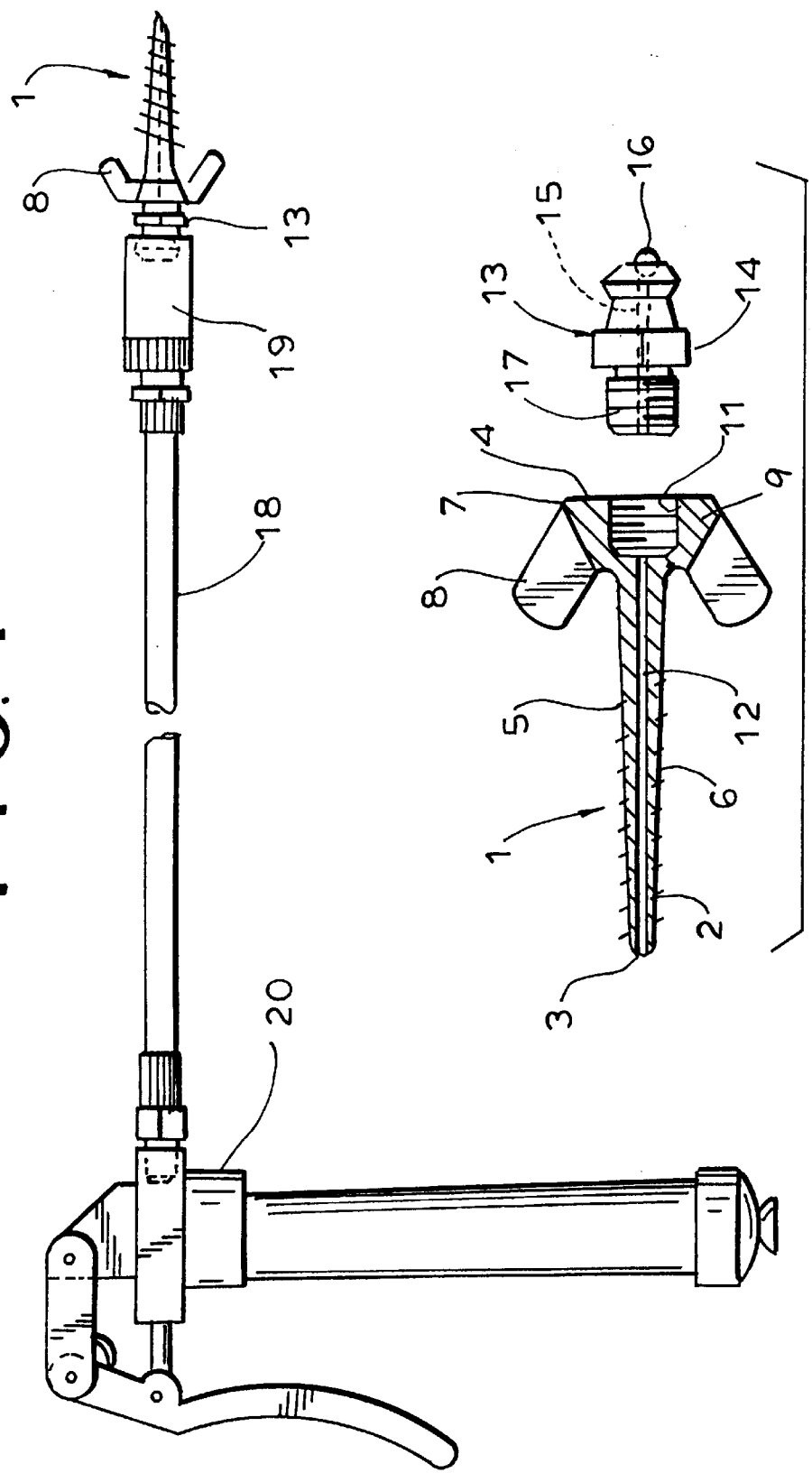

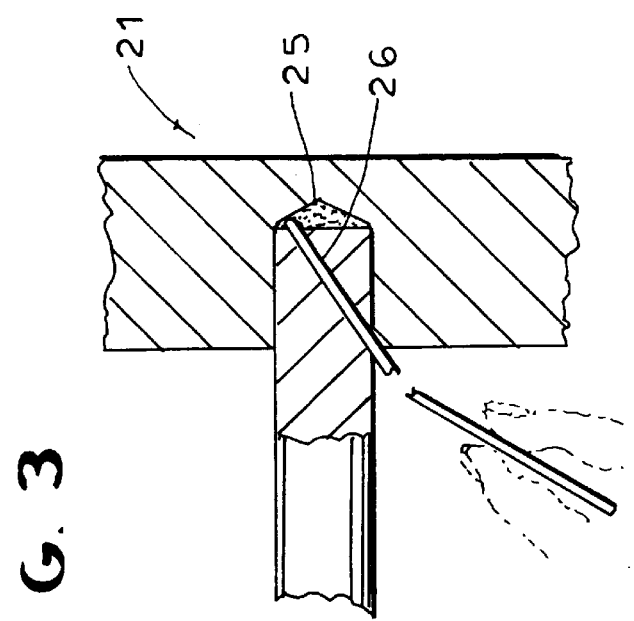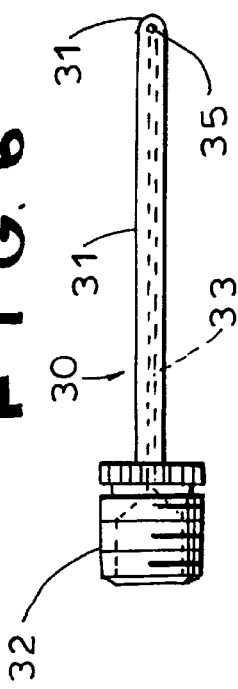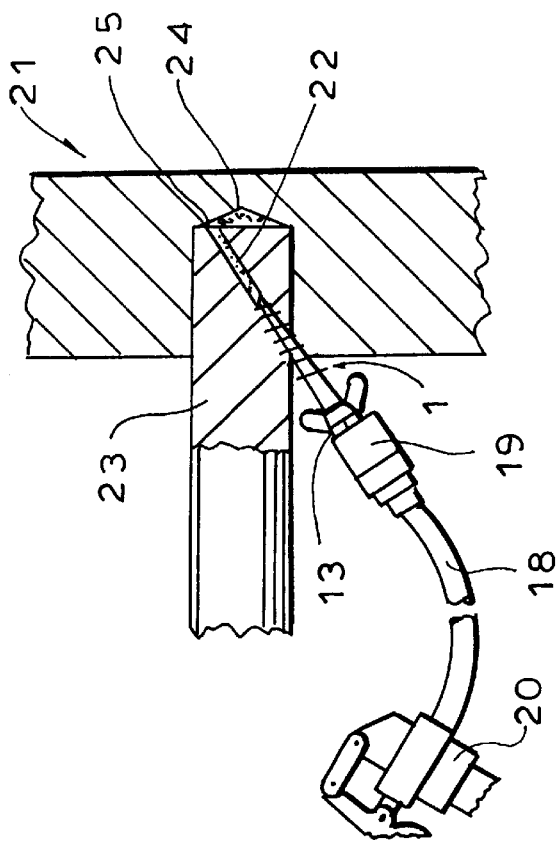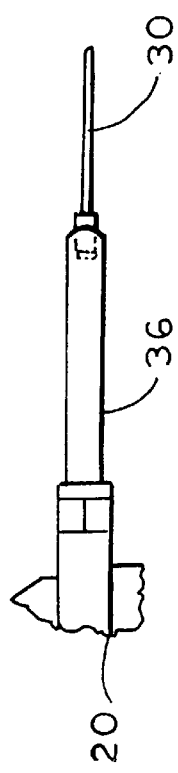

HIGH PRESSURE GLUE INJECTION DEVICE

This continuation-in-part of U.S. application Ser. No. 08/544,557 filed Oct. 18, 1995, now abandoned.

FIELD OF THE INVENTION

The invention relates to devices for applying glue under pressure to areas to be glued, particularly to areas which are relatively inaccessible, such as crevices, interstices etc. More specifically, the invention concerns a device for regluing leg joints in antique furniture which have "dried out" and weakened over time.

BACKGROUND OF THE INVENTION

When regluing a wooden joint, for example, several important practical considerations arise. It is clearly desirable that the glue be applied under high pressure to insure that all small interstices of the joint are completely filled with fresh glue and that the glue be relatively quick drying, which usually requires a glue of relatively high viscosity, in turn increasing the pressure required for application. At the same time, relatively simple, wholly manually operated tools are desirable to maintain low costs and avoid need for a power source. Such tools should also be relatively compact and handy to use in confined spaces, as access to furniture joints can be very limited.

U.S. Pat. No. 2,040,126 issued to Grieve in 1935 teaches a procedure for regluing tenon and mortise joints in which a small pilot hole is bored through the tenon and a needle shaped nozzle of a glue gun is inserted into the hole and a charge of glue is forced therethrough to flow between the mortise and tenon in an attempt to fill the gaps therebetween.

However, the patent teaches the use of a manually operated, syringe-type gun which cannot apply a very high pressure to force the viscous glue through the small hole, limiting the speed and effectiveness of application. In addition, any attempt to increase the injection pressure in the prior device would increase the risk of glue being forced back along the hole between the pilot hole wall the nozzle exterior also limiting the effective pressure of glue application in the joint.

A later U.S. Pat. No. 3,352,336, issued to Smith in 1967, teaches a manually operated glue injector having a piston shaft threadingly attached to the glue reservoir cylinder and a nozzle having a self cutting thread which provides a seal with the pilot hole wall, so that rotation of the piston shaft enables a higher glue injection pressure to be obtained while the self cutting thread seals the pilot hole, obviating risk of glue leakage back along the hole past the nozzle as a result of back pressure.

However, clearly, the entire process is relatively slow as the entire gun carrying the glue must, at each joint, be carefully screwed into the hole and subsequently unscrewed therefrom, while the manual rotation of the piston required to obtain the higher pressure is also a relatively slow procedure increasing undesirably the application or set up time. This is particularly significant when all joints of one or more articles of furniture are to be reglued as, either the gun must carry only sufficient charge for a single application, which requires a time consuming refilling step for each joint, or the glue must remain in the gun for a relatively long period, undesirable with fast setting glues.

Furthermore, manipulating the entire gun adjacent the joint can prove inconvenient, as the gun is relatively cumbersome.

Needle-form nozzles currently used for regluing veneers are generally too short and of large diameter so that it is often difficult to penetrate the layers properly, while the bores are so large that they often become plugged with splinters.

SUMMARY OF THE INVENTION

It is an object of the invention to obviate or ameliorate at least some of the above-mentioned disadvantages.

According to one aspect, the invention provides an adaptor for injecting glue dispensed under high pressure from a glue gun into a furniture joint to reglue the joint comprising an elongate body with leading, penetrating and rear, connecting ends, the body having a pointed penetrating shank which tapers outward as it extends rearward from the leading end and is formed with an external self-tapping screw thread and a fingerpiece protruding radially outward adjacent the rear end and an internal glue passageway extending axially completely through the body communicating with leading and rear ends. The rear end is provided with threading for attachment to a zerk attached to a glue outlet of the gun so that, with the zerk attached to the rear end, the leading end can be manually screwed into sealing engagement with a bore tapped into the furniture joint and an outlet hose of the grease gun secured to the zerk. Glue can then be dispensed under high pressure from the gun through the adaptor into the joint to fill and seal the joint.

The fingerpiece may comprise a pair of radially outwardly protruding wings.

According to another aspect, the invention provides a furniture repairer's kit including a set of such devices for use in regluing a variety of articles including wooden furniture joints and lamination.

This enables a lever operated, hydraulic action, gun known for greasing automobiles and which is widely available at low cost to be used for regluing operations to apply glue rapidly under very high pressure (e.g 7,500 psi).

Furthermore, as the adapters have fingerpieces they may, with zerks attached, readily be screwed by hand into pilot holes predrilled for all joints before the application of glue and the trigger action hydraulic gun fully charged with glue and connected with a known hose with a zerk coupling then simply pressed to each zerk sequentially.

This procedure minimizes the set up time which both permits a quick drying glue of desirably high viscosity to be used and improves the overall speed and efficiency of the regluing operation.

According to another aspect, the invention provides a furniture repairer's kit including a set of such devices for use in regluing a variety of articles including wooden furniture joints and veneer.

BRIEF DESCRIPTION OF THE DRAWINGS

A specific embodiment of the invention will now be described with reference to the accompanying drawings in which:

FIG. 1 is an elevational view, partly in cross-section, of an adaptor and zerk exploded apart for clarity;

FIG. 2 is an elevational view, partly in cross-section, of a joint regluing device according to the invention injecting glue into a furniture joint;

FIG. 3 is an elevational view, partly in cross-section, of a reglued joint having a dowel inserted and broken off in the pilot hole bored therein to plug the pilot hole;

FIG. 4 is an elevational view, of a gun of known type connected by a flexible hose to zerk screw fitted in a rear end of the adaptor;

FIG. 5 is a fragmentary, elevational view, of the gun connected by a pipe fitting to an alternative needle of known type for use in regluing veneer, and, FIG. 6 is an elevational view, of the needle shown in FIG. 5.

DESCRIPTION OF PARTICULAR EMBODIMENT

As shown in FIGS. 1–3, the adaptor 1 comprises an elongate, steel body 2 with leading, penetrating and rear, connecting ends, 3 and 4, respectively, and a pointed penetrating shank 5 which tapers outward as it extends rearward from the leading end 3 and is formed with an external, self-tapping screw thread 6. A fingerpiece 7 comprises a pair of wings 8 protruding radially outward and forward from a radially enlarged hub portion 9 having an internal screw thread for attachment to a zerk 11. An axial glue passageway 12 is bored completely through the body so as to communicate with leading and rear ends.

The adaptor has been made by made by boring a central passageway in a screw and silver soldering a wing nut to the head thereof. However, the adapter may be manufactured by casting in one piece of stainless steel and the passageway bored therethrough by a laser drilling procedure.

The zerk 13 is of the well known type widely used as a grease nipples and comprises a steel body 14 having a central bore 15 with spring loaded non return ball valve 16 at an inlet end and an externally threaded connecting portion 17 at an outlet end for connection to the adaptor.

The zerk 13 enables connection, via a known pressure adaptor hose 18 and coupler 19, to a high pressure, manually operated, hydraulic action gun 20 widely used for greasing automobiles.

As shown in FIG. 2 and 3, when regluing a mortise and tenon joint 21, a pilot hole 22 is first bored through the tenon 23 into communication with the (empty) interstice 24 of the joint and the adapter 1, fitted with the zerk 13, manually screwed therein. The gun 20 carrying a glue charge is then connected to the zerk 13 via the sleeve form coupling on the flexible hose 18 forming a press fit with the zerk and the gun lever pumped repeatedly to inject glue 25 under pressure into the joint. When a trace of glue first appears on the outside of the joint indicating that the joint is completely filled, the adapter is removed and the pilot hole plugged with a dowel 26 which is then broken off manually to length. The high pressure helps to ensure that even the smallest crevices are filled with glue. As mentioned above, when several joints are to be reglued, adapters fitted with zerks are first screwed into respective pilot holes and the gun charged with sufficient glue for all, applied to each in turn, thereby minimizing the time the glue remains in the gun, facilitating use of faster drying glues.

As shown in FIGS. 5 and 6, a stainless steel nozzle 30 for regluing veneer comprises an elongate body having a needle-form penetrating portion 31 and a radially enlarged, connecting portion 32 and an internal glue passageway 33 extending axially completely through the body between the opposite ends, the penetrating portion 31 having a rounded tip 34 and being further formed adjacent the tip with radially extending glue exit bores 35 communicating with the passageway 33.

In use the needle form nozzle 30 is connected to the gun 20 by a known rigid pipe fitting 36. The relatively small diameter and increased length (twice as long as those previously used) enables it to be slipped under loose veneer more easily and to penetrate further than prior needle type nozzles. The smaller bore resists clogging and plugging by wooden splinters while the radially extending bores enable the glue to spread over a larger area more speedily and evenly than prior nozzle type needles.

The adapter is not restricted in use to wooden articles. It may also be used to inject glue into masonry, stone and mortar.

A restorer's boxed kit enabling regluing both of veneers and joints comprises at least four adapters 1 with 3/32 twist threads, a corresponding number of zerks 13, one lever action hydraulic gun 20, one rigid pipe fitting 36, one 12 inch. flexible pressure hose 18 and coupling 19, one veneer needle 30 and a bunch of wooden dowels.

All components other than the adapters 1, dowels 26 and veneer needles, are sold by K-P Manufacturing Co, Minneapolis and displayed in their current (1994) catalogue in a variety of suitable models. For example, grease nipples/fittings or zerks of different angles (models no 3-5331, 2, 4, 5, 7 etc); flexible hoses with zerk couplers (e.g. model no 32011) and connection pipes, high pressure guns (model no 35574).

Veneer needles, sold as inflating needles, model no 3197, by National Industries Corporation, Lowell Mich.

Thus, the invention maximizes use of existing tooling of proven effectiveness in relation to high pressure grease lubrication and which is available at relatively low cost.

I claim:

1. An adaptor for injecting glue dispensed under high pressure from a glue gun into a furniture joint to reglue the joint comprising an elongate body with leading, penetrating and rear, connecting ends, the body having a pointed penetrating shank which tapers outward as it extends rearward from the leading end and is formed with an external self-tapping screw thread and a fingerpiece protruding radially outward adjacent the rear end comprising a pair of wings which protrude forward while diverging in opposite radial directions and an internal glue passageway extending axially completely through the body communicating with leading and rear ends, the rear end being provided with means for attachment to a zerk attached to a glue outlet of the gun so that, with the zerk attached to the rear end, the leading end can be manually screwed into sealing engagement with a bore tapped into the furniture joint and an outlet hose of the grease gun secured to the zerk so that glue dispensed under high pressure from the gun will be injected through the adaptor into the joint to fill and seal the joint.

2. A kit for repairing and restoring furniture by the injection of glue under high pressure to reglue the furniture comprising a hydraulic, trigger action grease gun, a flexible hose, four zerks, a supply of plug forming dowels and four adapters, each adaptor comprising an elongate body with leading, penetrating and rear, connecting ends, the body having a pointed penetrating shank which tapers outward as it extends rearward from the leading end and is formed with an external screw thread and a fingerpiece protruding radially outward adjacent the rear end and an internal glue passageway extending axially completely through the body communicating with leading and rear ends, the rear end being formed with an internal screw thread for attachment to a zerk so that all four adapters each with a zerk attached to a rear end can be manually screwed into sealing engagement with bores tapped into four supporting leg joints and the outlet hose of the grease gun secured to each zerk and sequentially hose and glue dispensed under high pressure from the gun injected through the adapters sequentially into the respective joints to fill and seal the joints, the adapters unscrewed from the respective bores and the bores plugged with respective dowels.

3. A kit according to claim 2 further including a nozzle for regluing veneer comprising an elongate body having a needle-form penetrating end and a radially enlarged, connecting end, and an internal glue passageway extending axially completely through the body communicating with the penetrating and connecting ends, the penetrating end being further formed adjacent the tip with radially extending glue exit bores communicating with the passageway, and a rigid pipe for connecting the needle to an outlet of the glue gun.

4. In combination, an adaptor for injecting glue dispensed under high pressure from a glue gun into a furniture joint to reglue the joint and a zerk, the adaptor comprising an elongate body with leading, penetrating and rear, connecting ends, the body having a pointed penetrating shank which tapers outward as it extends rearward from the leading end and is formed with an external self-tapping screw thread and a fingerpiece comprising a pair of wings protruding radially outward adjacent the rear end and an internal glue passageway extending axially completely through the body communicating with leading and rear ends, the rear end being provided with an internal screw thread meshing with a complementary thread on the zerk to attach the zerk to the rear end thereof so that, when the zerk is attached to the glue outlet of the glue gun and to the rear end of the adaptor, the leading end can be manually screwed into sealing engagement with a bore tapped into the furniture joint and an outlet hose of the grease gun secured to the zerk so that glue dispensed under high pressure from the gun will be injected through the adaptor into the joint to fill and seal the joint.

5. The combination of claim 4 in which the wings are forwardly divergent as they protrude outward.

6. A kit for repairing and restoring furniture by the injection of glue under high pressure to reglue the furniture comprising a hydraulic, trigger action grease gun operating at 7,500 P.S.I.; a flexible outlet hose for the grease gun, a zerk, and at least one adaptor comprising an elongate body with leading, penetrating and rear, connecting ends, the body having a pointed penetrating shank which tapers outward as it extends rearward from the leading end and is formed with an external screw thread and a fingerpiece protruding radially outward adjacent the rear end and an internal glue passageway extending axially completely through the body communicating with leading and rear ends, the rear end being formed with an internal screw thread for attachment to the zerk so that the adapter with a zerk attached to a rear end can be manually screwed into sealing engagement with a bore tapped into a joint to be reglued and the outlet hose of the grease gun secured to the zerk and glue dispensed under high pressure from the gun injected through the adapters the joint to fill and seal the joint, the adapter unscrewed from the bore and the bore fitted with a plug.

7. A kit according to claim 6 further comprising a supply of plug forming dowels.

8. A kit according to claim 6 in which the fingerpiece comprises a pair of radially outwardly protruding wings.

9. A kit according to claim 6 in which the fingerpiece comprises a pair of radially outwardly and forwardly diverging wings.

* * * * *